(12) United States Patent
Franer et al.

(10) Patent No.: US 8,672,890 B2
(45) Date of Patent: Mar. 18, 2014

(54) TROCAR SEAL WITH REDUCED CONTACT AREA

(75) Inventors: Paul T. Franer, Cincinnati, OH (US); Thomas A. Gilker, Cincinnati, OH (US); Cesar E. Moreno, Jr., Cincinnati, OH (US); Rosemarie Elefante, Loveland, OH (US); Daniel J. Mumaw, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 176 days.

(21) Appl. No.: 13/168,040

(22) Filed: Jun. 24, 2011

(65) Prior Publication Data

US 2011/0257598 A1    Oct. 20, 2011

Related U.S. Application Data

(63) Continuation of application No. 11/952,464, filed on Dec. 7, 2007, now Pat. No. 7,976,501.

(51) Int. Cl.
*A61M 5/178* (2006.01)
*A61M 25/00* (2006.01)

(52) U.S. Cl.
USPC ............... 604/167.02; 604/167.06; 604/264; 604/164.01

(58) Field of Classification Search
USPC ............. 604/264, 164.01, 167.01–167.06
See application file for complete search history.

(56) References Cited

U.S. PATENT DOCUMENTS

| | | |
|---|---|---|
| 3,900,022 A | 8/1975 | Widran |
| 3,903,877 A | 9/1975 | Terada |
| 3,924,608 A | 12/1975 | Mitsui |
| 3,980,078 A | 9/1976 | Tominaga |
| 3,981,276 A | 9/1976 | Ernest |
| 4,204,563 A | 5/1980 | Pyle |

(Continued)

FOREIGN PATENT DOCUMENTS

| | | |
|---|---|---|
| CA | 2060930 A1 | 10/1992 |
| DE | 10330518 A1 | 2/2005 |

(Continued)

OTHER PUBLICATIONS

International Search Report, dated Sep. 12, 2008.

(Continued)

*Primary Examiner* — Nicholas Lucchesi
*Assistant Examiner* — Rebecca E Eisenberg
(74) *Attorney, Agent, or Firm* — Nutter McClennen & Fish LLP

(57) ABSTRACT

Seal assemblies or valves, generally for use in trocar assemblies, are provided for reducing the amount of contact between an instrument being passed into and out of a trocar assembly and an inner surface of a sealing wall of such seal assemblies or valves. In one exemplary embodiment a valve includes an activation extension that is formed on the inner surface of the sealing wall of the valve and is configured such that a distal end of the sealing wall is moved to the open position by an instrument contacting the activation extension. In one embodiment the instrument does not come into contact with the inner surface of the sealing wall during the procedure. In another embodiment a distal-most end of the activation extension can be closer to a longitudinal axis extending through the flange than the inner surface of the sealing wall.

22 Claims, 14 Drawing Sheets

(56) References Cited

U.S. PATENT DOCUMENTS

| | | |
|---|---|---|
| 4,279,246 A | 7/1981 | Chikama |
| 4,687,033 A | 8/1987 | Furrow et al. |
| 4,690,140 A | 9/1987 | Mecca |
| 4,722,000 A | 1/1988 | Chatenever |
| 4,836,187 A | 6/1989 | Iwakoshi et al. |
| 4,877,016 A | 10/1989 | Kantor et al. |
| 4,909,798 A | 3/1990 | Fleischhacker et al. |
| 4,919,305 A | 4/1990 | Podgers |
| 4,943,280 A | 7/1990 | Lander |
| 5,084,057 A | 1/1992 | Green et al. |
| 5,104,383 A | 4/1992 | Shichman |
| 5,127,909 A | 7/1992 | Shichman |
| 5,141,498 A | 8/1992 | Christian |
| 5,167,220 A | 12/1992 | Brown |
| 5,180,373 A | 1/1993 | Green et al. |
| 5,191,878 A | 3/1993 | Iida et al. |
| 5,197,955 A | 3/1993 | Stephens et al. |
| 5,201,714 A | 4/1993 | Gentelia et al. |
| 5,207,213 A | 5/1993 | Auhll et al. |
| 5,209,737 A | 5/1993 | Ritchart et al. |
| 5,226,891 A | 7/1993 | Bushatz et al. |
| 5,237,984 A | 8/1993 | Williams, III et al. |
| 5,279,542 A | 1/1994 | Wilk |
| 5,312,363 A | 5/1994 | Ryan et al. |
| 5,312,397 A | 5/1994 | Cosmescu |
| 5,313,934 A | 5/1994 | Wiita et al. |
| 5,320,610 A | 6/1994 | Yoon |
| 5,326,013 A | 7/1994 | Green et al. |
| 5,330,437 A | 7/1994 | Durman |
| 5,334,164 A | 8/1994 | Guy et al. |
| 5,337,730 A | 8/1994 | Maguire |
| 5,339,800 A | 8/1994 | Wiita et al. |
| 5,342,315 A | 8/1994 | Rowe et al. |
| 5,347,988 A | 9/1994 | Hori |
| 5,354,302 A | 10/1994 | Ko |
| 5,364,002 A | 11/1994 | Green et al. |
| 5,369,525 A | 11/1994 | Bala et al. |
| 5,382,297 A | 1/1995 | Valentine et al. |
| 5,389,081 A | 2/1995 | Castro |
| 5,391,154 A | 2/1995 | Young |
| 5,392,766 A | 2/1995 | Masterson et al. |
| 5,395,342 A | 3/1995 | Yoon |
| 5,400,767 A | 3/1995 | Murdoch |
| 5,419,309 A | 5/1995 | Biehl |
| 5,441,513 A | 8/1995 | Roth |
| 5,443,452 A | 8/1995 | Hart et al. |
| 5,448,990 A | 9/1995 | De Faria-Correa |
| 5,449,370 A | 9/1995 | Vaitekunas |
| 5,458,633 A | 10/1995 | Bailey |
| 5,460,616 A | 10/1995 | Weinstein et al. |
| 5,462,100 A | 10/1995 | Covert et al. |
| 5,464,008 A | 11/1995 | Kim |
| 5,476,475 A | 12/1995 | Gadberry |
| 5,486,154 A | 1/1996 | Kelleher |
| 5,492,304 A | 2/1996 | Smith et al. |
| 5,496,280 A | 3/1996 | Vandenbroek et al. |
| 5,496,345 A | 3/1996 | Kieturakis et al. |
| 5,496,411 A | 3/1996 | Candy |
| 5,514,084 A | 5/1996 | Fisher |
| 5,514,153 A | 5/1996 | Bonutti |
| 5,518,026 A | 5/1996 | Benjey |
| 5,518,502 A | 5/1996 | Kaplan et al. |
| 5,533,496 A | 7/1996 | De Faria-Correa et al. |
| 5,535,759 A | 7/1996 | Wilk |
| 5,536,234 A | 7/1996 | Newman |
| 5,542,931 A | 8/1996 | Gravener et al. |
| 5,545,142 A | 8/1996 | Stephens et al. |
| 5,545,179 A | 8/1996 | Williamson, IV |
| 5,549,543 A | 8/1996 | Kim |
| 5,551,448 A | 9/1996 | Matula et al. |
| 5,554,151 A | 9/1996 | Hinchliffe |
| 5,568,828 A | 10/1996 | Harris |
| 5,569,183 A | 10/1996 | Kieturakis |
| 5,569,205 A | 10/1996 | Hart et al. |
| 5,575,756 A | 11/1996 | Karasawa et al. |
| 5,584,850 A | 12/1996 | Hart et al. |
| 5,590,697 A | 1/1997 | Benjey et al. |
| 5,603,702 A | 2/1997 | Smith et al. |
| 5,605,175 A | 2/1997 | Bergsma et al. |
| 5,628,732 A | 5/1997 | Antoon, Jr. et al. |
| 5,630,795 A | 5/1997 | Kuramoto et al. |
| 5,634,911 A | 6/1997 | Hermann et al. |
| 5,643,301 A | 7/1997 | Mollenauer |
| 5,647,372 A | 7/1997 | Tovey et al. |
| 5,647,840 A | 7/1997 | D'Amelio et al. |
| 5,651,757 A | 7/1997 | Meckstroth |
| 5,657,963 A * | 8/1997 | Hinchliffe et al. .......... 251/149.1 |
| 5,658,273 A | 8/1997 | Long |
| 5,685,823 A | 11/1997 | Ito et al. |
| 5,688,222 A | 11/1997 | Hluchy et al. |
| 5,709,664 A | 1/1998 | Vandenbroek et al. |
| 5,720,756 A | 2/1998 | Green et al. |
| 5,720,759 A | 2/1998 | Green et al. |
| 5,725,477 A | 3/1998 | Yasui et al. |
| 5,725,478 A | 3/1998 | Saad |
| 5,743,884 A | 4/1998 | Hasson et al. |
| 5,752,938 A | 5/1998 | Flatland et al. |
| 5,755,252 A | 5/1998 | Bergsma et al. |
| 5,755,732 A | 5/1998 | Green et al. |
| 5,782,859 A | 7/1998 | Nicholas et al. |
| 5,788,676 A | 8/1998 | Yoon |
| 5,792,044 A | 8/1998 | Foley et al. |
| 5,792,113 A | 8/1998 | Kramer et al. |
| 5,797,434 A | 8/1998 | Benjey et al. |
| 5,807,338 A | 9/1998 | Smith et al. |
| 5,814,026 A | 9/1998 | Yoon |
| 5,817,061 A | 10/1998 | Goodwin et al. |
| 5,848,992 A | 12/1998 | Hart et al. |
| 5,860,458 A | 1/1999 | Benjey et al. |
| 5,871,440 A | 2/1999 | Okada |
| 5,882,345 A | 3/1999 | Yoon |
| 5,902,231 A | 5/1999 | Foley et al. |
| 5,902,264 A | 5/1999 | Toso et al. |
| 5,906,595 A | 5/1999 | Powell et al. |
| 5,954,635 A | 9/1999 | Foley et al. |
| 5,964,781 A | 10/1999 | Mollenauer et al. |
| 5,983,958 A | 11/1999 | Bergsma et al. |
| 6,004,326 A | 12/1999 | Castro et al. |
| 6,007,487 A | 12/1999 | Foley et al. |
| 6,017,333 A | 1/2000 | Bailey |
| 6,062,276 A | 5/2000 | Benjey et al. |
| 6,063,050 A | 5/2000 | Manna et al. |
| 6,093,176 A | 7/2000 | Dennis |
| 6,110,103 A | 8/2000 | Donofrio |
| 6,126,592 A | 10/2000 | Proch et al. |
| 6,152,871 A | 11/2000 | Foley et al. |
| 6,159,182 A | 12/2000 | Davis et al. |
| 6,162,170 A | 12/2000 | Foley et al. |
| 6,167,920 B1 | 1/2001 | Enge |
| 6,176,823 B1 | 1/2001 | Foley et al. |
| 6,176,825 B1 | 1/2001 | Chin et al. |
| 6,206,057 B1 | 3/2001 | Benjey et al. |
| 6,206,822 B1 | 3/2001 | Foley et al. |
| 6,216,661 B1 | 4/2001 | Pickens et al. |
| 6,217,509 B1 | 4/2001 | Foley et al. |
| 6,253,802 B1 | 7/2001 | Enge |
| 6,264,604 B1 | 7/2001 | Kieturakis et al. |
| 6,287,313 B1 | 9/2001 | Sasso |
| 6,354,992 B1 | 3/2002 | Kato |
| 6,371,909 B1 | 4/2002 | Hoeg et al. |
| 6,409,657 B1 | 6/2002 | Kawano |
| 6,423,266 B1 | 7/2002 | Choperena et al. |
| 6,425,535 B1 | 7/2002 | Akiba |
| 6,425,859 B1 | 7/2002 | Foley et al. |
| 6,443,190 B1 | 9/2002 | Enge |
| 6,447,446 B1 | 9/2002 | Smith et al. |
| 6,482,181 B1 | 11/2002 | Racenet et al. |
| 6,494,893 B2 | 12/2002 | Dubrul et al. |
| 6,497,687 B1 | 12/2002 | Blanco |
| 6,516,835 B2 | 2/2003 | Enge |
| 6,520,907 B1 | 2/2003 | Foley et al. |
| 6,534,002 B1 | 3/2003 | Lin et al. |
| 6,551,282 B1 | 4/2003 | Exline et al. |
| 6,562,046 B2 | 5/2003 | Sasso |

(56) References Cited

U.S. PATENT DOCUMENTS

| | | |
|---|---|---|
| 6,569,120 B1 | 5/2003 | Green et al. |
| 6,595,915 B2 | 7/2003 | Akiba |
| 6,595,946 B1 | 7/2003 | Pasqualucci |
| 6,601,617 B2 | 8/2003 | Enge |
| 6,605,098 B2 | 8/2003 | Nobis et al. |
| 6,638,214 B2 | 10/2003 | Akiba |
| 6,648,906 B2 | 11/2003 | Lasheras et al. |
| 6,679,833 B2 | 1/2004 | Smith et al. |
| 6,679,834 B2 | 1/2004 | Stahl et al. |
| 6,679,837 B2 | 1/2004 | Daikuzono |
| 6,699,185 B2 | 3/2004 | Gminder et al. |
| 6,702,787 B2 | 3/2004 | Racenet et al. |
| 6,712,757 B2 | 3/2004 | Becker et al. |
| 6,726,663 B1 | 4/2004 | Dennis |
| 6,755,782 B2 | 6/2004 | Ogawa |
| 6,860,892 B1 | 3/2005 | Tanaka et al. |
| 6,918,924 B2 | 7/2005 | Lasheras et al. |
| 6,923,759 B2 | 8/2005 | Kasahara et al. |
| 6,942,671 B1 | 9/2005 | Smith |
| 6,981,966 B2 | 1/2006 | Green et al. |
| 6,989,003 B2 | 1/2006 | Wing et al. |
| 7,008,416 B2 | 3/2006 | Sakaguchi et al. |
| 7,025,747 B2 | 4/2006 | Smith |
| 7,052,454 B2 | 5/2006 | Taylor |
| 7,056,321 B2 | 6/2006 | Pagliuca et al. |
| 7,077,803 B2 | 7/2006 | Kasahara et al. |
| 7,083,626 B2 | 8/2006 | Hart et al. |
| 7,104,657 B2 | 9/2006 | Sherwin |
| 7,105,009 B2 | 9/2006 | Johnson et al. |
| 7,112,185 B2 | 9/2006 | Hart et al. |
| 7,163,525 B2 | 1/2007 | Franer |
| 7,198,598 B2 | 4/2007 | Smith et al. |
| 7,207,347 B2 | 4/2007 | Olshanetsky et al. |
| 7,976,501 B2 | 7/2011 | Franer et al. |
| 2002/0022762 A1 | 2/2002 | Beane et al. |
| 2002/0065450 A1 | 5/2002 | Ogawa |
| 2002/0068923 A1 | 6/2002 | Caldwell et al. |
| 2002/0103420 A1 | 8/2002 | Coleman et al. |
| 2002/0161387 A1 | 10/2002 | Blanco |
| 2003/0004529 A1 | 1/2003 | Tsonton et al. |
| 2003/0130674 A1 | 7/2003 | Kasahara et al. |
| 2003/0139756 A1 | 7/2003 | Brustad |
| 2003/0195472 A1 | 10/2003 | Green et al. |
| 2004/0034339 A1 | 2/2004 | Stoller et al. |
| 2004/0106942 A1 | 6/2004 | Taylor et al. |
| 2004/0167559 A1 | 8/2004 | Taylor et al. |
| 2004/0220452 A1 | 11/2004 | Shalman |
| 2004/0230161 A1 | 11/2004 | Zeiner |
| 2004/0256004 A1 | 12/2004 | Kessell et al. |
| 2005/0033342 A1 | 2/2005 | Hart et al. |
| 2005/0043683 A1 | 2/2005 | Ravo |
| 2005/0059865 A1 | 3/2005 | Kahle et al. |
| 2005/0059934 A1 | 3/2005 | Wenchell et al. |
| 2005/0070946 A1 | 3/2005 | Franer et al. |
| 2005/0077688 A1 | 4/2005 | Voegele et al. |
| 2005/0077689 A1 | 4/2005 | Hueil |
| 2005/0096605 A1 | 5/2005 | Green et al. |
| 2005/0131349 A1 | 6/2005 | Albrecht et al. |
| 2005/0165277 A1 | 7/2005 | Carrillo et al. |
| 2005/0203543 A1 | 9/2005 | Hilal et al. |
| 2005/0216028 A1 | 9/2005 | Hart et al. |
| 2005/0241647 A1 | 11/2005 | Nguyen et al. |
| 2005/0288622 A1 | 12/2005 | Albrecht et al. |
| 2006/0020165 A1 | 1/2006 | Adams |
| 2006/0047240 A1 | 3/2006 | Kumar et al. |
| 2006/0052666 A1 | 3/2006 | Kumar et al. |
| 2006/0068360 A1 | 3/2006 | Boulais |
| 2006/0069312 A1 | 3/2006 | O'Connor |
| 2006/0100485 A1 | 5/2006 | Arai et al. |
| 2006/0122556 A1 | 6/2006 | Kumar et al. |
| 2006/0122557 A1 | 6/2006 | Kumar et al. |
| 2006/0135972 A1 | 6/2006 | Zeiner |
| 2006/0135977 A1 | 6/2006 | Thompson et al. |
| 2006/0135978 A1 | 6/2006 | Franer |
| 2006/0149137 A1 | 7/2006 | Pingleton et al. |
| 2006/0199998 A1 | 9/2006 | Akui et al. |
| 2006/0211916 A1 | 9/2006 | Kasahara et al. |
| 2006/0235455 A1 | 10/2006 | Oshida |
| 2006/0276688 A1 | 12/2006 | Surti |
| 2006/0293559 A1 | 12/2006 | Grice et al. |
| 2007/0021713 A1 | 1/2007 | Kumar et al. |
| 2007/0129719 A1 | 6/2007 | Kendale et al. |
| 2007/0142709 A1 | 6/2007 | Martone et al. |
| 2007/0149931 A1 | 6/2007 | Cannon et al. |
| 2007/0149993 A1 | 6/2007 | Kasahara et al. |
| 2007/0185453 A1 | 8/2007 | Michael et al. |
| 2007/0191759 A1 | 8/2007 | Stoller et al. |
| 2007/0204890 A1 | 9/2007 | Torii |
| 2007/0225566 A1 | 9/2007 | Kawanishi |
| 2007/0244361 A1 | 10/2007 | Ikeda et al. |
| 2009/0005799 A1 | 1/2009 | Franer et al. |
| 2009/0149813 A1 | 6/2009 | Franer et al. |

FOREIGN PATENT DOCUMENTS

| | | |
|---|---|---|
| EP | 0344907 | 12/1989 |
| EP | 0517248 | 12/1992 |
| EP | 0567142 | 10/1993 |
| EP | 568383 A1 | 11/1993 |
| EP | 570802 A1 | 11/1993 |
| EP | 664101 A1 | 7/1995 |
| EP | 0696459 A1 | 2/1996 |
| EP | 731718 A1 | 9/1996 |
| EP | 845960 A1 | 6/1998 |
| EP | 0873721 | 10/1998 |
| EP | 875256 A1 | 11/1998 |
| EP | 890342 A1 | 1/1999 |
| EP | 898971 A2 | 3/1999 |
| EP | 0972493 A2 | 1/2000 |
| EP | 1210904 A2 | 6/2002 |
| EP | 1284664 A1 | 2/2003 |
| EP | 1312318 A1 | 5/2003 |
| EP | 1323373 A2 | 7/2003 |
| EP | 1348386 A1 | 10/2003 |
| EP | 1350477 | 10/2003 |
| EP | 1459688 A1 | 9/2004 |
| EP | 1629787 A1 | 7/2006 |
| EP | 1679043 A1 | 7/2006 |
| EP | 1698291 A1 | 9/2006 |
| EP | 1707133 A1 | 10/2006 |
| EP | 1707135 A1 | 10/2006 |
| EP | 1709918 | 10/2006 |
| EP | 1834571 A1 | 9/2007 |
| EP | 1834573 A1 | 9/2007 |
| EP | 1997446 | 12/2008 |
| JP | 61036718 A | 2/1986 |
| JP | 3106329 A | 5/1991 |
| JP | 4020324 A | 1/1992 |
| JP | 4158825 A | 6/1992 |
| JP | 4170929 A | 6/1992 |
| JP | 4329510 A2 | 11/1992 |
| JP | 5192294 A | 8/1993 |
| JP | 5199979 A | 8/1993 |
| JP | 5207962 A | 8/1993 |
| JP | 6133927 A | 5/1994 |
| JP | 6169879 A | 6/1994 |
| JP | 6304121 A | 11/1994 |
| JP | 7178039 A | 7/1995 |
| JP | 7246187 A | 9/1995 |
| JP | 7289501 A | 11/1995 |
| JP | 7313442 A | 12/1995 |
| JP | 8154888 A | 6/1996 |
| JP | 8173372 A | 7/1996 |
| JP | 10043128 A | 2/1998 |
| JP | 11146882 A | 6/1999 |
| JP | 2002224014 A | 8/2002 |
| JP | 2002238906 A | 8/2002 |
| JP | 2003284686 A | 10/2003 |
| JP | 2004016455 A | 1/2004 |
| JP | 2004267583 A | 9/2004 |
| JP | 2005253543 A | 9/2005 |
| JP | 2005319101 A2 | 11/2005 |
| WO | WO-9407552 A1 | 4/1994 |
| WO | WO-9532019 | 11/1995 |

(56) References Cited

FOREIGN PATENT DOCUMENTS

| | | |
|---|---|---|
| WO | WO-9604946 A1 | 2/1996 |
| WO | WO-9740759 A1 | 11/1997 |
| WO | WO-0189371 A1 | 11/2001 |
| WO | WO-0230305 | 4/2002 |
| WO | WO-02078527 A2 | 10/2002 |
| WO | WO-02096307 A2 | 12/2002 |
| WO | WO-03011154 A2 | 2/2003 |
| WO | WO-2004043275 A1 | 5/2004 |
| WO | WO-2005016133 A1 | 2/2005 |
| WO | WO-2005097019 A2 | 10/2005 |
| WO | WO-2005097234 A2 | 10/2005 |
| WO | WO-2009005986 A1 | 1/2009 |

OTHER PUBLICATIONS

PCT International Search Report dated Mar. 24, 2009.

* cited by examiner

TROCAR SEAL WITH REDUCED CONTACT AREA

CROSS REFERENCE TO RELATED APPLICATIONS

This application is a continuation of U.S. patent application Ser. No. 11/952,464 filed on Dec. 7, 2007 and entitled "Trocar Seal with Reduced Contact Area," which is hereby incorporated by reference in its entirety.

FIELD OF THE INVENTION

This application relates to trocar assemblies, and more particularly to seal assemblies or valves often used in trocar assemblies.

BACKGROUND OF THE INVENTION

Surgical procedures often require a surgeon to gain access to a cavity in a patient's body. Generally, when such a procedure is required, an incision is made in an exterior wall of the cavity and an instrument is inserted into the working channel created by the incision. One common instrument used in such a procedure is a trocar assembly. Trocar assemblies include a variety of components, but generally can include a trocar cannula, a trocar obturator, and a trocar housing. In many designs, in order to access the body cavity, the trocar cannula is directed through the skin and the trocar obturator is inserted through an interior lumen defined by the cannula. The trocar obturator is then used to penetrate the skin, which has often already had an incision made in it with a scalpel or similar device, and access the body cavity. More specifically, in some designs, applying pressure against a proximal end of the trocar obturator allows a sharp point at a distal end of the trocar obturator to be forced through the skin until it enters the body cavity. Then, the trocar cannula is inserted through the perforation made by the trocar obturator and the trocar obturator is withdrawn, leaving the inner lumen of the trocar cannula as a path to access the body cavity from outside of the body.

The trocar housing can be joined to a proximal end portion of the trocar cannula, and further, the housing can define a working chamber with an open distal end portion that is in communication with the interior lumen of the cannula. Just as the interior lumen can receive the obturator, it can also receive other elongated surgical instruments such that the instruments can be axially extended into and withdrawn from the cannula through the proximal end portion of the working chamber defined by the trocar housing. For example, in order to allow a surgeon to more easily see during a procedure, an endoscope can be inserted through the cannula and proximal or into the body cavity.

It is common for a sealing assembly or sealing device to be used in the trocar assembly. Sealing assemblies and devices are often generally referred to as valves. Sealing assemblies generally help prevent fluid or gas from escaping during surgical procedures. Such prevention is needed, especially during certain minimally invasive surgical procedures, in which an insufflation gas is used to expand a body cavity. However, it can be difficult to maintain the internal gas pressure because during the course of the procedure instruments are typically passed into and out of the trocar assembly. Accordingly, a sealing assembly, and often two sealing assemblies, are generally provided in the trocar assembly. The sealing assembly can seal against an outer surface of inserted instruments and thus can prevent fluids and insufflation gas from leaving and/or entering the body cavity through the trocar cannula.

In instances where two sealing assemblies are provided, the one that is a top, or proximal, seal is usually designed to seal around a surgical instrument when it is present, and the bottom, or distal, seal is usually designed for sealing the trocar cannula when the instrument is not present. One type of distal seal is a "duckbill" seal, which is sometimes referred to as a zero-closure valve. A duckbill seal assembly generally includes a pair of opposed valve members which open and close a seal face in much the same manner a duck opens and closes its bill. The opening and closing of the duckbill seal assembly can generally result from the insertion and/or removal of an instrument from the duckbill seal assembly. More specifically, the duckbill seal assembly can generally be opened by contacting an inner surface of the seal face with the instrument. Further, the valve members can include a straight wall angle which defines a flex point for the opening and closing of the assembly, or alternatively, they can include multi-angled walls that can serve the same purpose but that can also have improved tear resistance and buckling prevention. Some examples of such valve members can be found in United States Publication No. 2005/0077688 of Voegele et al., filed on Sep. 17, 2004, and entitled "Multi-Angled Duckbill Seal Assembly," which is hereby incorporated by reference in its entirety. An inner surface of each of the valve members and the seal face is generally in contact with an environment outside of the body cavity while an outer surface of each of the valve members and the seal face is generally in contact with an environment inside of the body cavity.

While such sealing assemblies are effective to prevent fluids and insufflation gas from leaving and/or entering the body cavity through the trocar cannula, fluid from both outside and inside the body cavity often builds up on both the inner and outer surfaces of the seal face, respectively. Thus, as instruments are passed through the sealing assemblies and come into contact with the seal face, fluid that exists on the inner and outer surfaces of the seal face is often wiped directly onto the instruments during the course of a procedure. This is especially problematic for instruments such as endoscopes and laparoscopes because fluid is often wiped directly onto the camera lens and thus obscures the surgeon's view.

Accordingly, there is a need for a seal assembly that reduces the amount of contact between instruments being passed into and out of the seal assembly and a seal face of such seal assembly.

SUMMARY OF THE INVENTION

Trocars are generally provided having one or more valves or seal assemblies provided to create a closed system between the outside environment and the environment in which the trocar is being inserted. In one embodiment a valve for use in a trocar assembly is provided and includes a valve having a flange with an aperture extending through the flange, a sealing wall extending distally from the flange and having an inner surface and a distal end that is movable between a sealed closed position and an open position, and an activation extension formed on the sealing wall and configured such that the distal end of the sealing wall is moved to the open position by an instrument contacting the activation extension. In the open position the sealing wall can be configured to receive an instrument therethrough. In an exemplary embodiment the instrument does not come into contact with the distal end of the sealing wall during the procedure. The instrument can also not contact the inner surface of the sealing wall during the procedure. The activation extensions can have a height and a width. In one embodiment a distal-most end of the activation extension can be closer to a longitudinal axis extending through the flange than the inner surface of the sealing wall. The distal-most end of the activation extension can be proximal to the distal end of the sealing wall. Further, the activation extension can come in the form of a protrusion on the inner surface and can have a substantially triangular profile. An angle formed by a contacting side of the substantially triangular profile of the activation extension and a transverse plane substantially perpendicular to a longitudinal axis extending through the flange can be more acute than an angle formed by the inner surface of the sealing wall and the same transverse plane.

In one embodiment the activation extension can be integrally formed with the sealing wall, while in another embodiment it can be made from a different material than the sealing wall. In an exemplary embodiment the material used to form the activation extension can be more rigid than the material used to form the sealing wall.

In various embodiments the sealing wall can be made of two or more seal elements, including embodiments with at least three seal elements and four seal elements. The two or more seal elements can include inner and outer surfaces and can meet at a seal face at the distal end of the sealing wall. Further, the activation extension can be a plurality of activation extensions and each activation extension can be separately disposed on the inner surface of a separate seal element of the two or more seal elements. At least one activation extension can be formed on the inner surface of each of the seal elements of the sealing wall. In one embodiment the inner surfaces of the seal elements can be configured to selectively promote movement of fluid away from a central portion of the seal elements toward a peripheral portion of the seal elements at the seal face. For instance, a central portion of each of the inner surfaces of the seal elements can be at a more proximal position than a peripheral portion of the seal elements at the seal face. In another embodiment, the inner surfaces of the seal elements can be configured to quickly evacuate fluid from a peripheral portion of the seal elements toward a central portion of the seal elements at, and subsequently beyond, the seal face. For instance, a peripheral portion of each of the inner surfaces of the seal elements can be at a more proximal position than a central portion of the seal elements at the seal face. The valve can be a duckbill seal assembly or a zero-closure valve.

In another embodiment of a valve for use in a trocar assembly, a sealing wall extends from a flange and is configured for selectively opening and closing to seal an opening of a trocar assembly when an instrument is not passed through the valve. The sealing wall can also include at least one activation extension protruding from an inner surface of the sealing wall. In an exemplary embodiment the sealing wall can be formed of a first material and an instrument contacting surface of the at least one activation extension can be formed of a second material. In a further exemplary embodiment the second material can be more rigid than the first material. The at least one activation extension can have a height and a width. When an instrument is passed through the valve, the assembly can be configured such that the instrument does not contact a distal end of the sealing wall. Alternatively, or additionally, the assembly can be configured such that when an instrument is passed through the valve, the instrument does not come into contact with the inner surface of the sealing wall. In another embodiment a distal-most end of the at least one activation extension can be closer to a longitudinal axis extending through the flange than the inner surface of the sealing wall. The distal-most end of the activation extension can be proximal to the distal end of the sealing wall.

In various embodiments the sealing wall can be made of two or more seal elements, including embodiments with at least three seal elements and four seal elements. The two or more seal elements can include inner and outer surfaces and can meet at a seal face at the distal end of the sealing wall. Further, the activation extension can be a plurality of activation extensions and each activation extension can be separately disposed on the inner surface of a separate seal element of the two or more seal elements. At least one activation extension can be formed on the inner surface of each of the seal elements of the sealing wall. In one embodiment the inner surfaces of the seal elements can be configured to selectively promote movement of fluid away from a central portion of the seal elements toward a peripheral portion of the seal elements at the seal face. For instance, a central portion of each of the inner surfaces of the seal elements can be at a more proximal position than a peripheral portion of the seal elements at the seal face. In another embodiment, the inner surfaces of the seal elements can be configured to quickly evacuate fluid from a peripheral portion of the seal elements toward a central portion of the seal elements at, and subsequently beyond, the seal face. For instance, a peripheral portion of each of the inner surfaces of the seal elements can be at a more proximal position than a central portion of the seal elements at the seal face. The valve can be a duckbill seal assembly or a zero-closure valve.

In one embodiment of a trocar assembly a housing is provided that includes two seals: a proximal instrument seal that is adapted to form a seal around an instrument inserted through the instrument seal and a distal zero-closure valve with an inner surface and a seal face. In an exemplary embodiment as least one ridge can be formed on the inner surface of the zero-closure valve. The at least one ridge can be adapted to prevent contact between an instrument inserted through the zero-closure valve and the seal face. The at least one ridge can also be adapted to prevent contact between an instrument inserted through the zero-closure valve and the inner surface. The at least one ridge can have a height and a width. The zero-closure valve can be configured to open in response to an instrument contacting the at least one ridge as the instrument is passed through the zero-closure valve. In one embodiment a distal-most end of the at least one ridge can be closer to a longitudinal axis extending through the zero-closure valve than the inner surface of the zero-closure valve. In various embodiments the zero-closure valve can include two or more seal elements, including embodiments with at least three seal elements and four seal elements. The two or more seal elements can include inner and outer surfaces and can meet at the seal face at a distal end of the zero-closure valve. Further, the at least one ridge can be a plurality of ridges and each ridge can be separately disposed on the inner surface of a separate seal element of the two or more seal elements. At least one ridge can be formed on the inner surface of each of the seal elements of the zero-closure valve. In one embodiment the inner surfaces of the seal elements can be configured to selectively promote movement of fluid away from a central portion of the seal elements toward a peripheral portion of the seal elements at the seal face. For instance, a central portion of each of the inner surfaces of the seal elements can be at a more proximal position than a peripheral portion of the seal elements at the seal face. In another embodiment, the inner surfaces of the seal elements can be configured to quickly evacuate fluid from a peripheral portion of the seal elements toward a central portion of the seal elements at, and subsequently beyond, the seal face. For instance, a peripheral portion of each of the inner surfaces of the seal elements can be at a more proximal position than a central portion of the seal elements at the seal face.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices disclosed herein. One or more examples of these embodiments are illustrated in the accompanying drawings. Those skilled in the art will understand that the devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The trocar described herein includes a seal assembly with a seal face that is configured to open without being contacted by an object, such as a surgical tool, e.g., an endoscope or laparoscope. More specifically, the seal face can be opened by a surgical tool contacting activation extensions that are associated with the seal assembly. Such contact with the activation extensions, as opposed to the seal face, can allow the object to pass through the seal face without ever contacting the seal face. This presents a number of advantages, including reducing the amount of fluid that comes into contact with the object and reducing the amount of drag on the object as it is passed in and out of the seal assembly during a surgical procedure.

Apart from the seal assembly, in accordance with the present disclosure, the general structure of the trocar assembly does not generally form part of the present invention. As such, a person skilled in the art will certainly appreciate that the present seal assembly can be adapted for use with a variety of trocar assemblies without departing from the spirit of the invention disclosed herein. Further, although the seal assembly as disclosed is generally described as being a duckbill seal assembly for a trocar assembly, a person skilled in the art will appreciate that the designs discussed herein can be equally applied to any seal assembly, not just duckbill seal assemblies, and other devices that utilize seal assemblies. A person skilled in the art will also appreciate that while the embodiments disclosed herein generally refer to the present seal assembly as a seal assembly, the seal assembly can also be described as a valve, or in some instances, a zero-closure valve.

Figure 1:
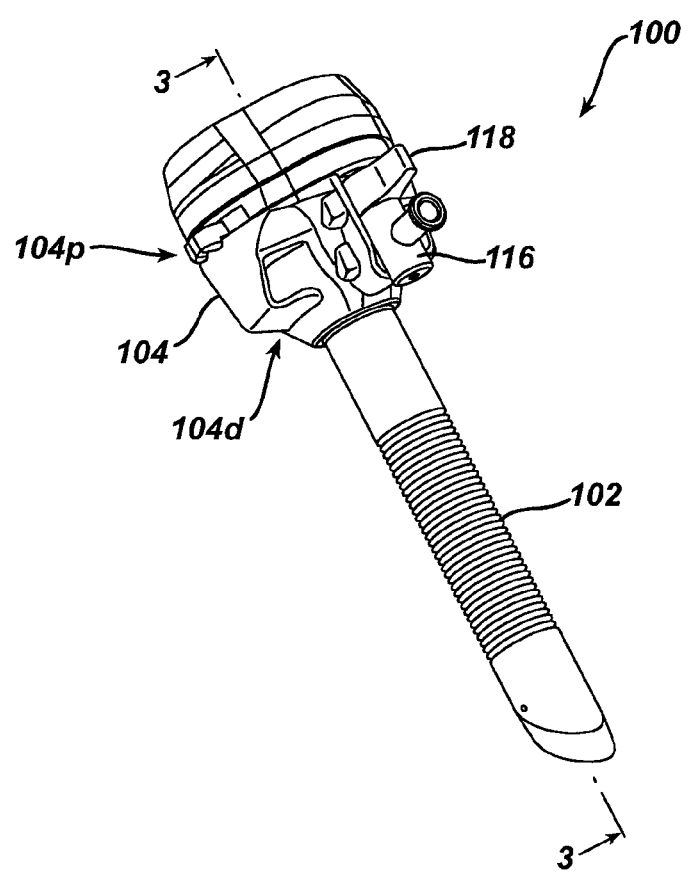
FIG. 1 is an isometric view of one exemplary embodiment of a trocar assembly.
Figure 2:
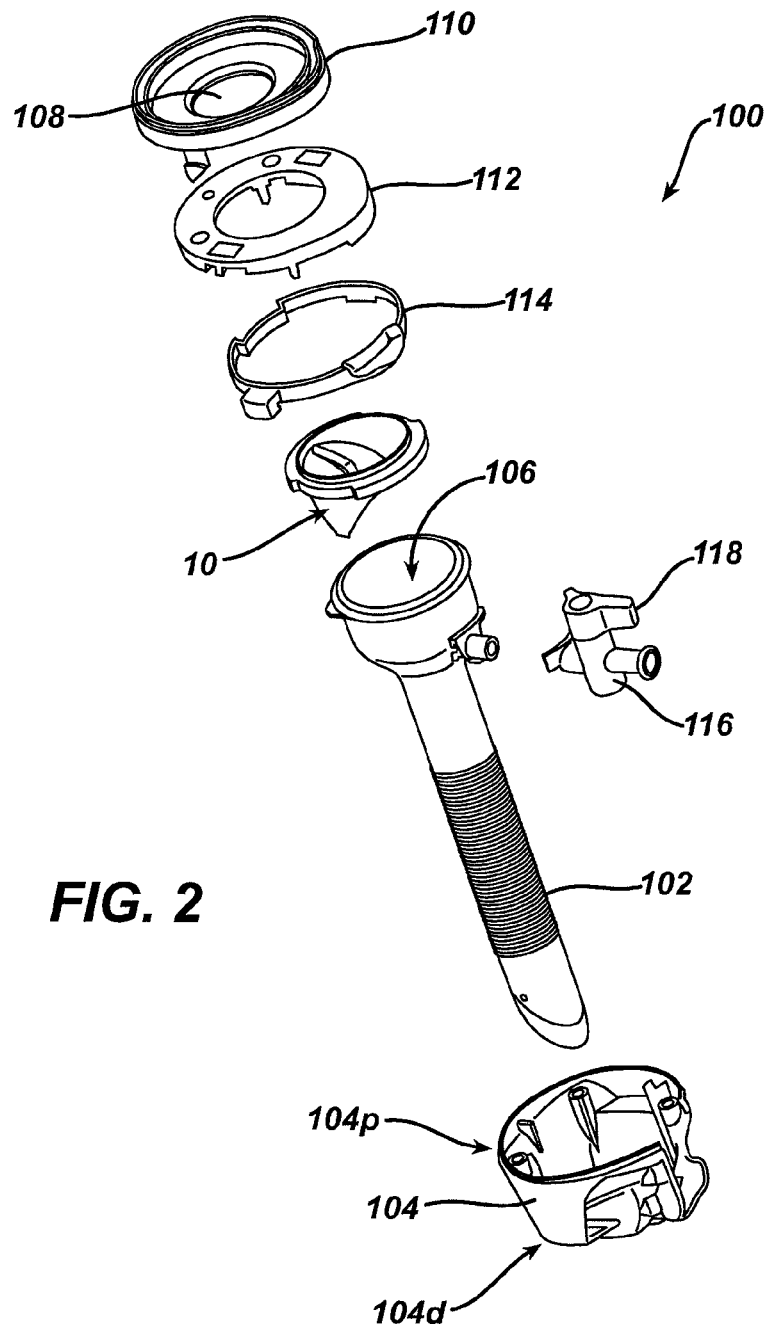
FIG. 2 is an isometric exploded view of the trocar assembly of FIG. 1 with one exemplary embodiment of a seal assembly.
Figure 3:
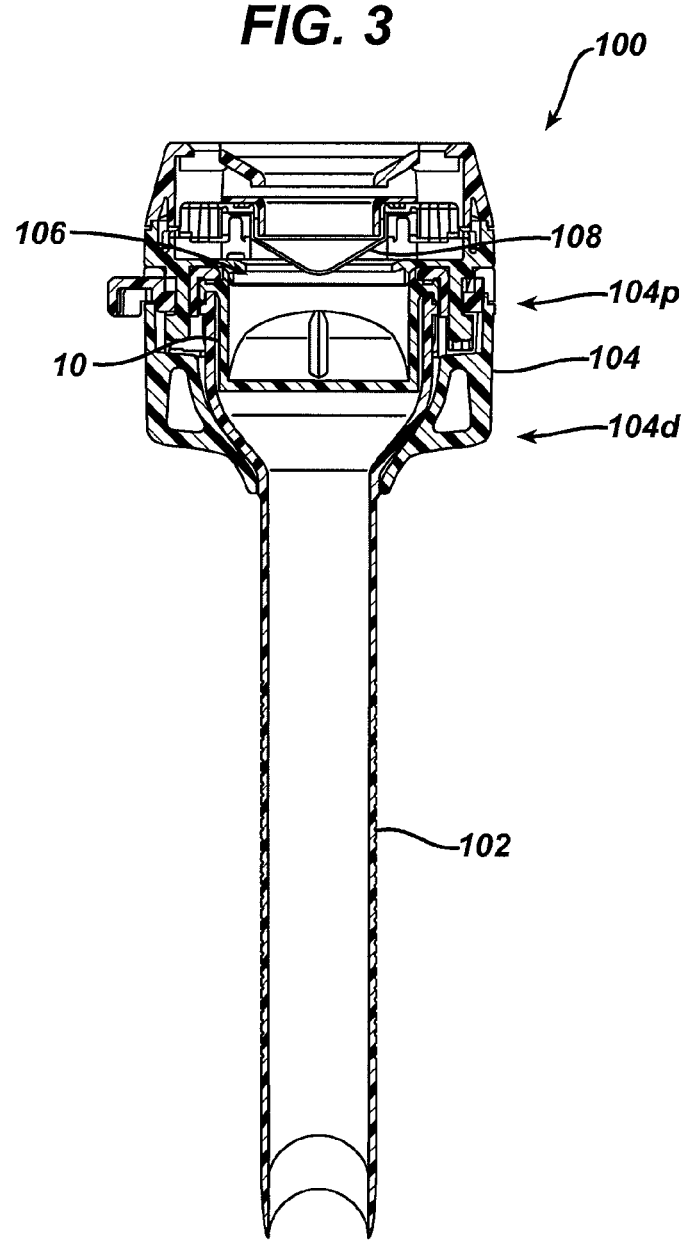
FIG. 3 is a side cross-sectional view of the trocar assembly of FIG. 1 taken at line 3-3.
Figure 4:
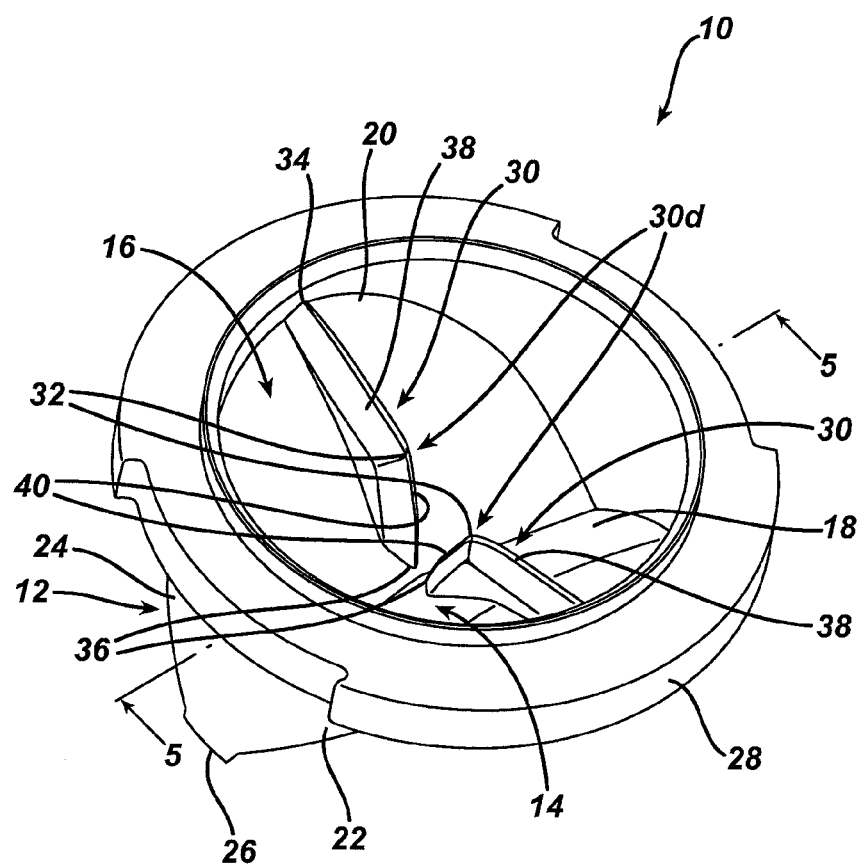
FIG. 4 is an isometric view of the exemplary embodiment of the seal assembly of FIG. 2.
Figure 5:
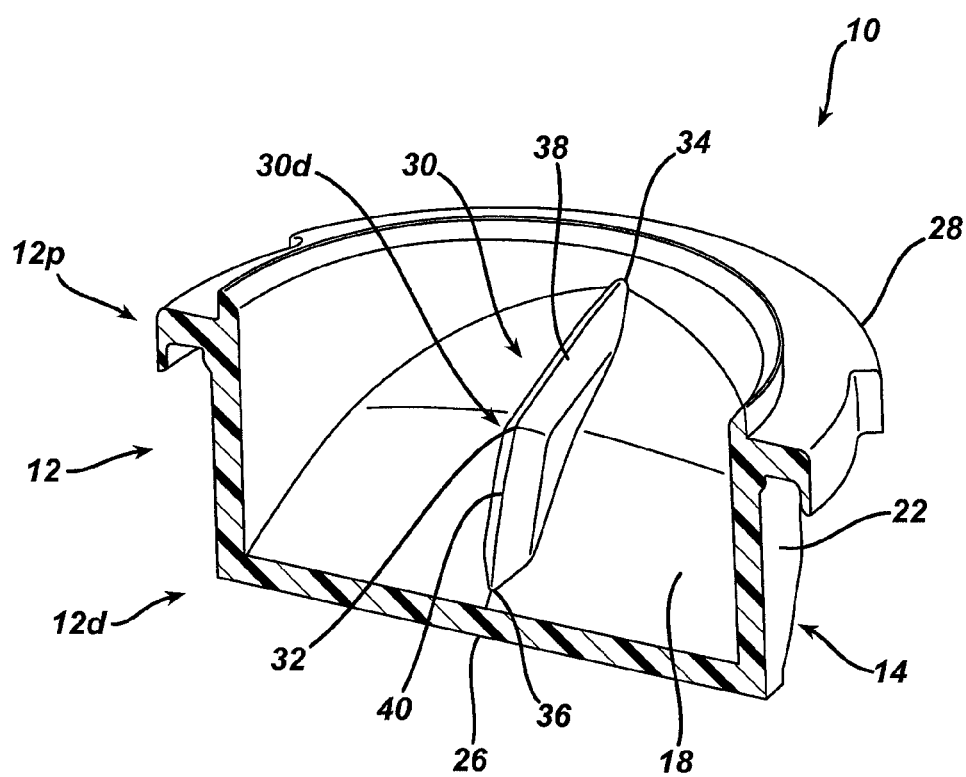
FIG. 5 is an isometric cross-sectional view of the seal assembly of FIG. 4 taken at line 5-5.
Figure 6:
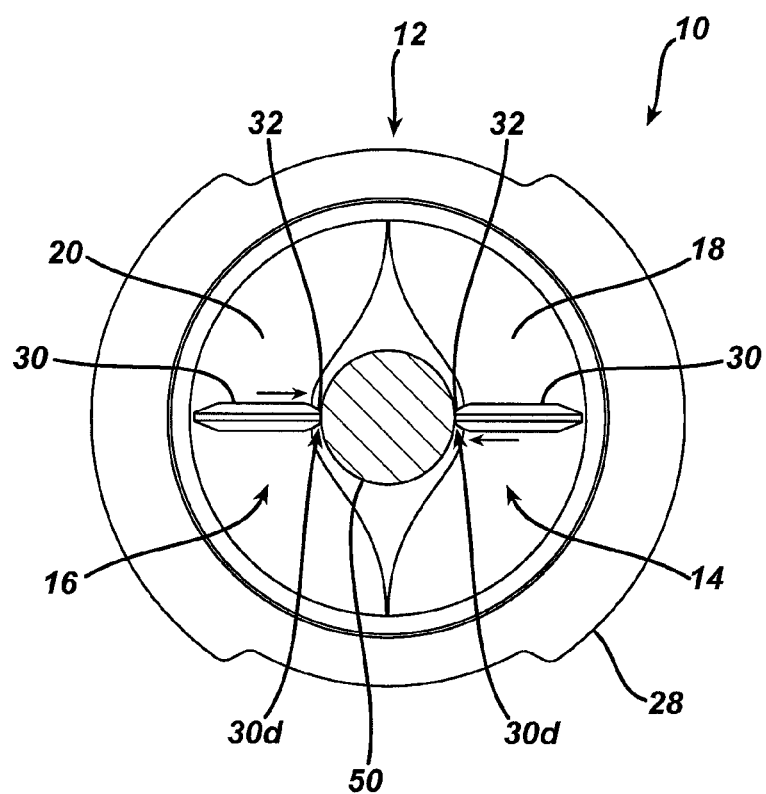
FIG. 6 is a top view of the exemplary embodiment of the seal assembly of FIG. 4.

Referring to FIGS. 1-3, a trocar assembly 100 can generally include a trocar cannula 102 and a trocar housing (or handle) 104. Further, the trocar cannula 102 can define an interior lumen with an open proximal end portion and an open distal end portion. The proximal end portion can extend into and be mounted in a distal end portion 104d of the trocar housing 104. The trocar housing 104 can optionally include an open proximal end portion 104p that can define a working channel 106. In one embodiment the working channel 106 can include a proximal seal assembly 108 at least partially positioned therein. In an exemplary embodiment the working channel 106 can further include a duckbill seal assembly 10 also at least partially positioned therein. As shown, for example, in FIG. 3, the duckbill seal assembly 10 is positioned distal to the proximal seal assembly 108 and allows for selective sealing of the working channel 106 of the trocar housing 104. A person skilled in the art will recognize that while in an exemplary embodiment two seal assemblies are provided in the working channel 106, in other embodiments one seal assembly, or more than two seal assemblies, can also be used in the trocar assembly 100. Further, the proximal seal assembly 108 and the duckbill seal assembly 10 can be secured into a desired position, at least partially within the working channel 106 in a variety of ways. In an exemplary embodiment, a crown ring 110 and a gasket ring 112 are snap-fit together and then the gasket ring 112 is secured to the trocar housing 104. A gasket retainer ring 114 can further secure the attachment between the gasket ring 112 and the trocar housing 104. In one embodiment the trocar housing 104 can further include a stop cock valve 116 and a stop cock valve lever 118, which can work together to allow and/or prevent passage of an insufflation fluid or gas, e.g. carbon dioxide, through flexible tubing into a portion of the trocar housing 104 and the trocar cannula 102.

The proximal seal assembly 108 can be adapted to cooperate with an exterior of any instrument inserted at least partially through the trocar cannula 102 such that the proximal seal assembly 108 can sealingly engage the exterior of the instrument and thus can prevent the passage of fluids through the trocar housing 104 when the instrument is present within the trocar assembly 100. A variety of instruments, although primarily surgical instruments, can be inserted at least partially through the trocar cannula 102. One example of such an instrument is an endoscope or a similar device that enables visualization and/or surgical procedures during minimally invasive surgical procedures. One skilled in the art will recognize that many other instruments are known for insertion into at least a portion of the trocar cannula 102, and accordingly, that the proximal seal assembly 108 can likewise sealingly engage the exterior of those instruments as well.

FIGS. 4-7 illustrate one embodiment of a duckbill seal assembly 10 that can be used with a device such as a trocar assembly. As shown, duckbill seal assembly 10 can generally include a seal body 12 with a proximal end 12p and a distal end 12d, a longitudinal axis L extending through the seal body 12, and a transverse plane P substantially perpendicular to the longitudinal axis L. The seal body 12 can be configured to selectively open and substantially close the seal assembly 10 in response to an object, such as instrument 50, being inserted into the seal body 12. In one embodiment the seal body 12 can be a unitary structure, such as a sealing wall. In another embodiment the seal body 12 can include a plurality of seal elements. The plurality of seal elements can also be described as two or more sealing walls. In one embodiment, the plurality of seal elements can be opposed. In the embodiment illustrated in FIGS. 4-7, two seal elements 14, 16 comprise the seal body 12. In other embodiments, discussed in further detail below, three or more seal elements can form the seal body 12. The seal elements 14, 16 can extend distally with respect to the transverse plane P from the proximal end 12p of the seal body 12. The seal elements 14, 16 can include inner surfaces 18, 20 and outer surfaces 22, 24, respectively, and in an exemplary embodiment the inner surfaces 18, 20 of the seal elements 14, 16 can meet at the distal end 12d of the seal body 12 to form a seal face 26. Further, the seal body 12 and/or the seal elements 14, 16 can generally be configured to selectively open and substantially close the seal face 26. In one embodiment the proximal end 12p of the seal body 12 can include a flange 28 extending beyond a width of the seal body 12. The flange 28 can be any shape, but in the illustrated embodiment the flange 28 is circumferential. In another embodiment the seal body 12 is the flange 28.

The seal assembly can also include one or more activation extensions. At least one activation extension can be formed on the inner surface of at least one seal element. In the embodiment illustrated in FIGS. 4-7, one activation extension 30 is formed on each of the two seal elements 14, 16. Activation extensions can be formed on each seal element, or alternatively, activation extensions can be formed on a select number of seal elements. In one embodiment the activation extension is a ridge.

The activation extensions 30 can be configured to open and substantially close the seal face 26, either in lieu of or in conjunction with the seal body 12 and/or the seal elements 14, 16. In an exemplary embodiment contact from an object, such as a surgical tool, with the activation extensions 30 can cause the seal face 26 to open. The portion of the activation extensions 30 that an object contacts is sometimes referred to as an instrument contacting surface. Such contact by an object can result in reduced contact between the object and the seal face 26. In fact, in an exemplary embodiment the object does not contact the seal face 26 as it extends toward and through the seal face 26.

Likewise, the contact between the activation extensions 30 and the object can also be reduced and/or minimized. Such reduced contact can be created by configuring the activation extensions 30 in a variety of ways. In an exemplary embodiment a point contact, which can be designated by an instance where the object and each of the activation extensions 30 engages only at a single point, can be created at distal-most ends 30d of the activation extensions 30. In other embodiments the contact can be characterized as a line contact such that only a small portion of the activation extensions, or a limited number of single points, engages the object. In one embodiment the distal-most ends 30d of the activation extensions 30 are closer to the longitudinal axis L than are the inner surfaces 18, 20. Further, the distal-most ends 30d of the activation extensions 30 can be proximal to the seal face 26. In other embodiments the distal-most ends 30d are more proximal to the longitudinal axis L than they are to the respective inner surfaces 18, 20. In still other embodiments a distance between the distal-most ends 30d and the inner surfaces 18, 20 is at least in the range of about 0.07 to 0.17 inches.

Each activation extension 30 can come in a variety of shapes and sizes, and furthermore, can be associated with any portion of the seal body 12 and/or the seal elements 14, 16. In an exemplary embodiment the activation extensions 30 have a substantially triangular profile. More particularly, the distal-most ends each form a first vertex 32 of the substantially triangular profile while second and third vertices 34, 36 are located near the proximal and distal ends 12p, 12d of the seal body 12, respectively, such that a majority of a profile of the inner surfaces 18, 20 are covered by the activation extensions 30. In other embodiments the activation extensions 30 only cover a portion of the profile of the inner surfaces 18, 20, and as such, the second and third vertices 34, 36 are closer together and not necessarily near either the proximal or distal ends 12p, 12d of the seal body 12.

Figure 7:
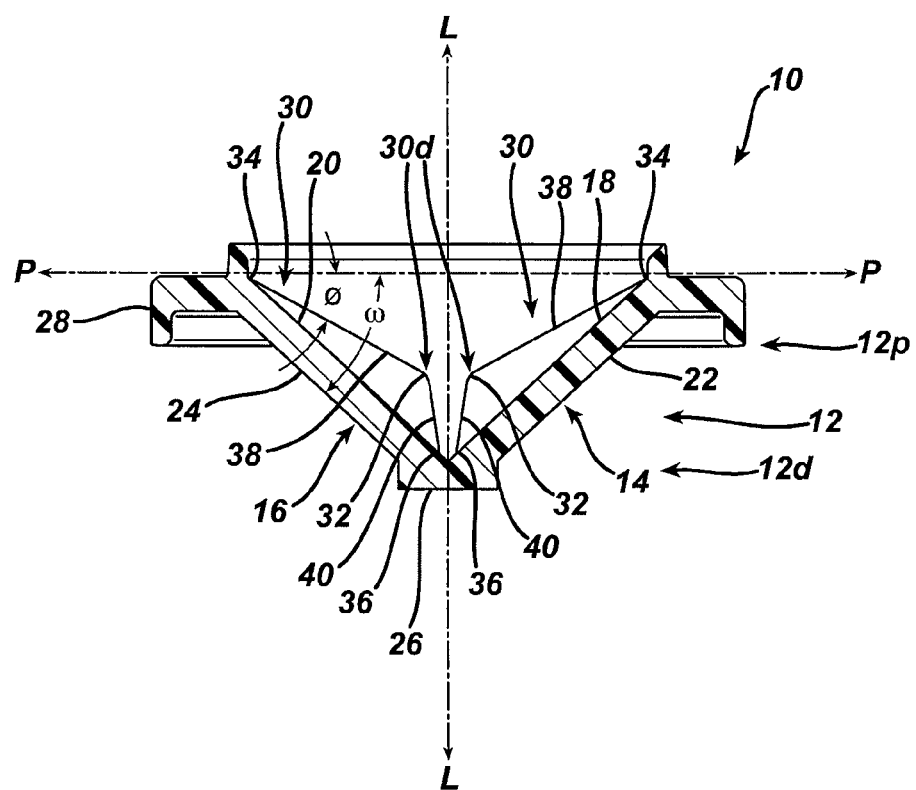
FIG. 7 is a side view of the exemplary embodiment of the seal assembly of FIG. 4.

With specific reference to FIG. 7, an angle Φ is formed between proximal surfaces 38 of each of the activation extensions 30, which can extend from the proximal end 12p of the seal body 12 to the distal-most end 30d of the activation extension 30, and the transverse plane P. As illustrated, the angle Φ is more acute than an angle ω formed between the each of the inner surfaces 18, 20 and the transverse plane P. In some embodiments the angle Φ can be in the range of about ten to seventy degrees more acute than the angle ω. In one embodiment the distal surfaces 40 of each of the activation extensions 30, which can extend from the distal-most end 30d of the activation extension 30 to the distal end 12d of the seal body 12, can be substantially parallel to the longitudinal axis L when the seal assembly 10 is in an initial position, prior to engaging the activation extensions 30 with an object. In other embodiments the distal surfaces 40 can be undercut such that the distal most-ends 30d of the activation extensions 30 are more proximal to the longitudinal axis L than the third vertices 36 of the activation extensions 30 when the seal assembly 10 is in the initial position.

Although the illustrated embodiment shows the profile of the activation extensions 30 being substantially triangular, in other embodiments the profile of the activation extensions 30 can be substantially quadrilateral, substantially pentagonal, or in any other shape known to those of skill in the art. Furthermore, the sizes, distances, and other numerical values discussed herein are easily adaptable depending on the size and shape of the seal assembly 10 in which the activation extensions 30 are being used. Accordingly, it is contemplated that even though a particular size and shape may not be discussed herein, it is easily ascertainable given the disclosure provided herein.

The activation extensions 30 can be formed in a variety of ways. In one embodiment the activation extensions 30 can be integrally formed with the seal body 12 and/or the seal elements 14, 16 from a single material. For example, the seal body 12 can be made of an elastomer, such as polyisoprene, and the activation extensions 30 can likewise be formed directly from the same elastomer such that the seal body 12 and the activation extension 30 form one unitary seal assembly 10. When the seal body 12 also includes seal elements 14, 16, the seal elements 14, 16 can be made of an elastomer, and again the activation extensions 30 can be formed from the same elastomer such that the seal body 12, the seal elements 14, 16, and the activation extensions 30 form one unitary seal assembly 10.

Figure 8:
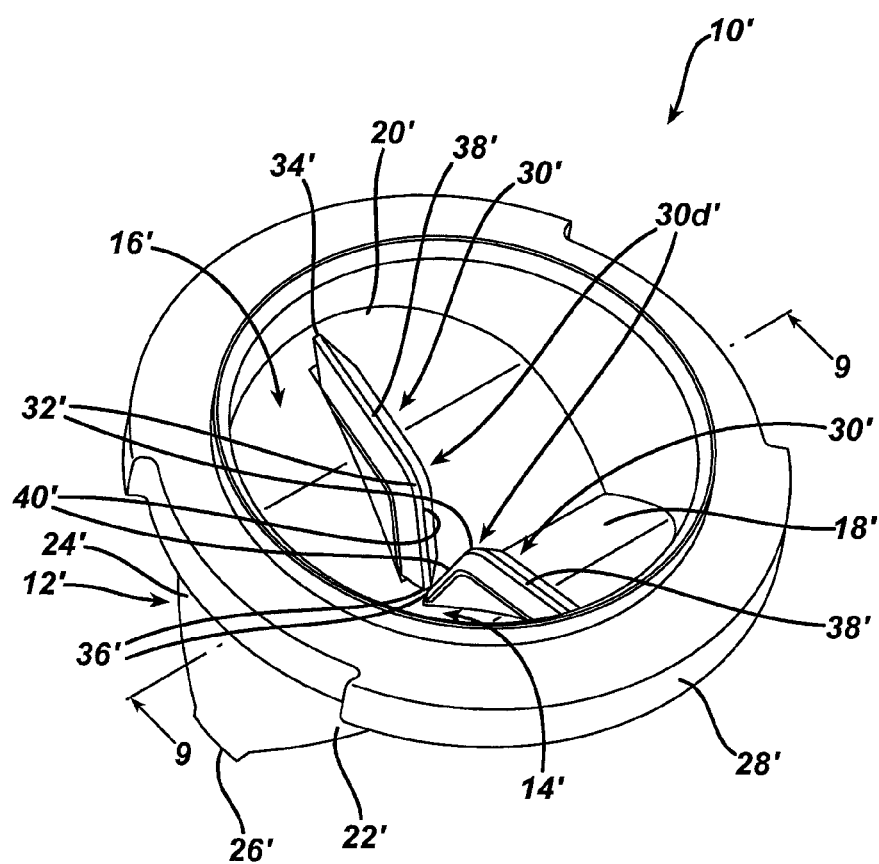
FIG. 8 is an isometric view of another exemplary embodiment of a seal assembly.
Figure 9:
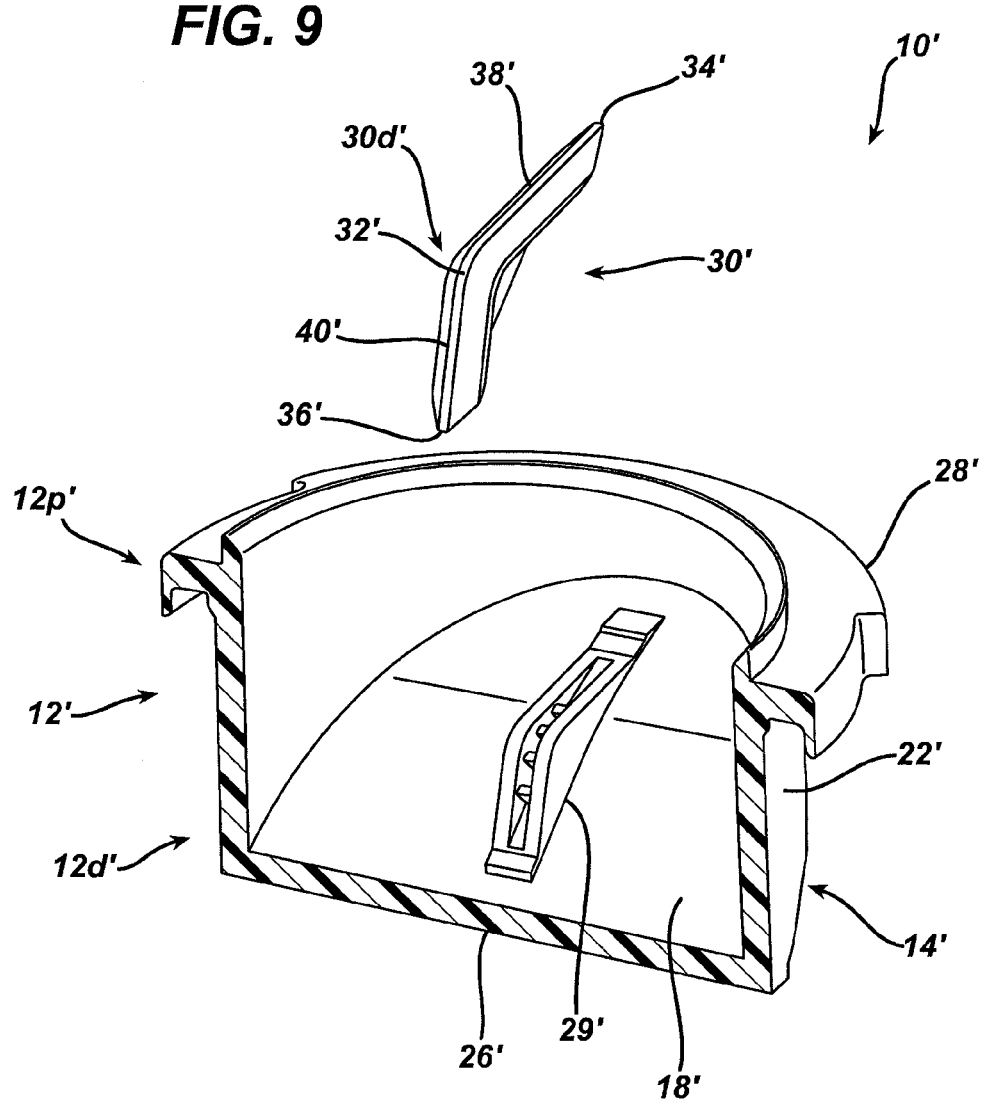
FIG. 9 is an isometric exploded cross-sectional view of the seal assembly of FIG. 8 taken at line 9-9.
Figure 10:
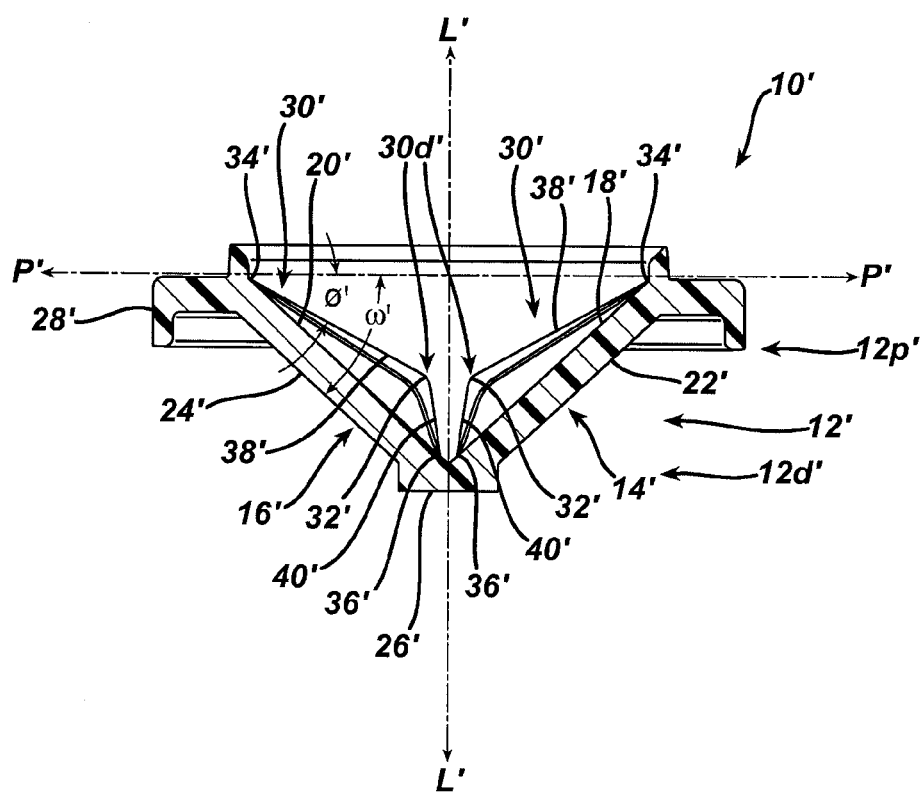
FIG. 10 is a side view of the exemplary embodiment of the seal assembly of FIG. 8.

Alternatively, as illustrated in FIGS. 8-10, in other embodiments activation extensions 30' can be a part of a seal assembly 10' by being mated to either a seal body 12' and/or seal elements 14', 16'. Furthermore, in embodiments where the seal elements 14', 16' include additional components, such as ribs 29' (as shown in FIG. 9), the activation extensions 30' can be configured to be mated to the additional component(s) in lieu of, or in addition to, the seal body 12' and/or the seal elements 14', 16'. A variety of mating techniques can be used to mate the activation extensions 30' to any portion of the seal assembly 10', but in an exemplary embodiment the activation extensions 30' are snap-fit to inner surfaces 18', 20' of the seal elements 14', 16'. One benefit that a snap-fit provides is that it can allow the activation extension 30' to be subsequently detached from the inner surfaces 18', 20'. This can be beneficial when different sized objects, and thus different sized activation extensions 30', may be desirable. In such an instance each activation extension can be specifically configured for use with a particular type and/or size object. In other embodiments the activation extensions 30' can be mated to any portion of the seal assembly 10', not just the inner surfaces 18', 20' of the seal elements 14', 16', and it can be done using a variety of techniques, including other means of mechanical attachment and/or by the use of adhesives.

Just as the activation extensions 30, 30' can be formed in a variety of ways, they can also be formed from a variety of materials. While in one embodiment the activation extensions 30, 30' can be made from the same material as the seal body 12, 12' and/or the seal elements 14, 14', 16, 16', in another embodiment a hybrid seal assembly can be formed. In the hybrid seal assembly at least two different materials are used to form the seal assembly 10, 10'. More particularly, the seal body 12, 12' and/or the seal elements 14, 14', 16, 16' can be made of one material and the activation extensions 30, 30' can be made from a different material. In one embodiment, only the instrument contacting surfaces of the activation extensions 30, 30' are made from a different material than the seal body 12, 12' and/or the seal elements 14, 14', 16, 16'. Alternatively, three or more materials can also be used to form different components of the hybrid seal assembly. In an exemplary embodiment the material(s) used for the activation extensions 30, 30', or at least the instrument contacting surfaces, is more rigid than the material(s) used to form the seal body 12, 12' and/or the seal elements 14, 14', 16, 16'. In some embodiments the activation extensions 30, 30' are configured such that any deformation of the activation extensions 30, 30' is limited and thus can be described as being rigid or semi-rigid. In one embodiment the activation extensions 30, 30' are made of polycarbonate. Regardless of the material used to make the activation extension 30, 30', the various techniques discussed above, as well as others known to those skilled in the art, can be used to form the hybrid seal assembly.

Figure 11A:
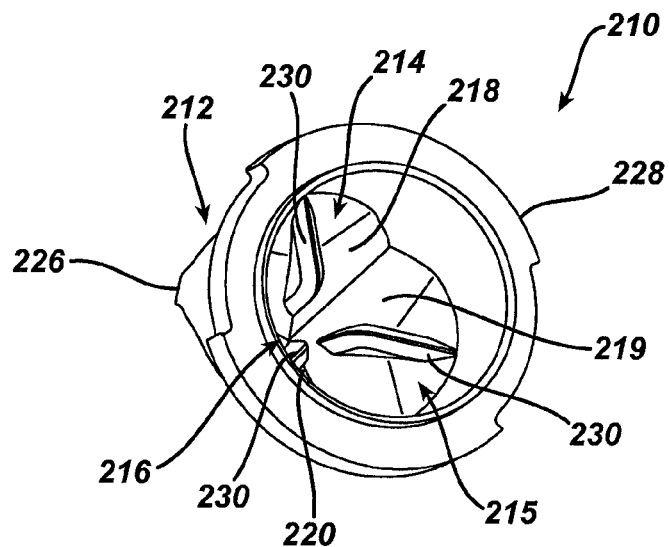
FIG. 11A is a top perspective view of another exemplary embodiment of a seal assembly.
Figure 11B:
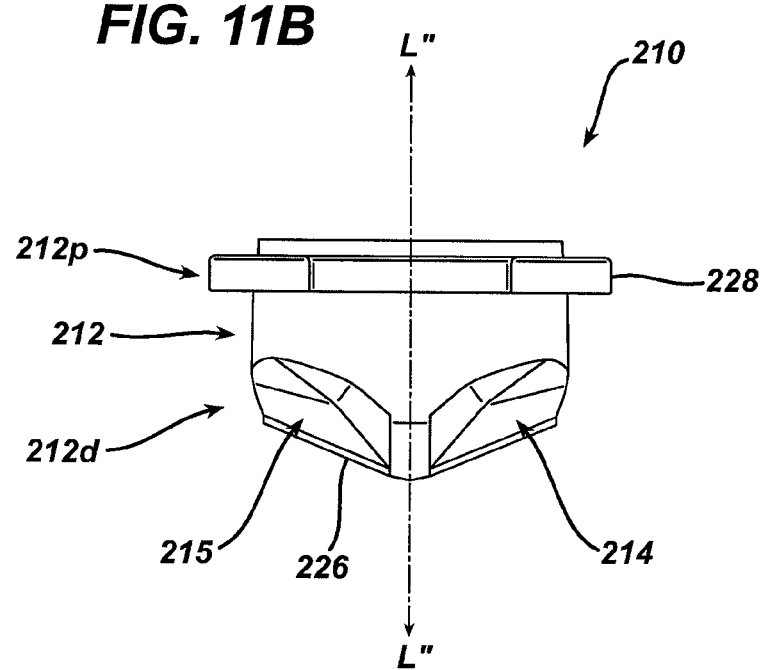
FIG. 11B is a side view of the exemplary embodiment of FIG. 11A.

FIGS. 11A and 11B illustrate an alternative embodiment of a seal assembly. Similar to previous embodiments, seal assembly 210 can generally include seal body 212 with a proximal end 212p and a distal end 212d, a longitudinal axis L" extending through the seal body 212, and a transverse plane substantially perpendicular to the longitudinal axis L". Seal assembly 210 can include any and all of the same characteristics and features as discussed above with respect to seal assemblies 10, 10', but while the previously illustrated embodiments included only two seal elements, seal assembly 210 includes three seal elements 214, 215, 216. The seal elements 214, 215, 216 can extend distally with respect to the transverse plane from the proximal end 212p of the seal body 212. The seal elements 214, 215, 216 can include inner surfaces 218, 219, 220 and outer surfaces and in an exemplary embodiment the inner surfaces 218, 219, 220 of the seal elements 214, 215, 216 can meet at the distal end 212d of the seal body 212 to form a seal face 226. Further, the seal body 212 and/or the seal elements 214, 215, 216 can generally be configured to selectively open and substantially close the seal face 226. In one embodiment the proximal end 212p of the seal body 212 can include a flange 228 extending beyond a width of the seal body 212.

The quick removal of fluid that can build-up in the seal assembly 210 can be further achieved by configuring the inner surfaces 218, 219, 220 of the seal elements 214, 215, 216 such that they can quickly evacuate fluid from the peripheral portion 213 of the seal body 212 and toward the central portion 213 of the seal body 212. While a variety of configurations can be used to achieve this design goal, in one embodiment the peripheral portion 213 can be positioned such that it is more proximal than the central portion 211. In other words, as illustrated in FIG. 11B, peripheral portion 213 is raised proximally relative to the central portion 211.

Similar to the seal assemblies 10, 10', the seal assembly 210 can also include one or more activation extensions. In the embodiment illustrated in FIGS. 11A and 11B, one activation extension 230 is formed on each of the three seal elements 214, 215, 216. Although it is not necessary that an activation extension be formed on each seal element, in an exemplary embodiment, the activation extensions 230 are symmetrically placed such that when an object is placed between the activation extensions 230, the object can be equally engaged around its perimeter. Further, the activations extensions 230 can include any and all of the characteristics and features discussed above with respect to activation extensions 30.

The use of three seal elements 214, 215, 216 as opposed to two seal elements can allow the seal face 226 to open more quickly, which in turn can provide a larger and longer lasting opening for fluid caught in the seal assembly 210 to exit the seal assembly 210 before an object closes the opening. The removal of fluid from the seal assembly 210 can be beneficial because it reduces the amount of fluid that comes into contact with an object being inserted into the seal assembly 210. This is particularly important when using devices such as endoscopes and laparoscopes because the lens used by the surgeon to view the surgical site should be clear and smudge-free.

Figure 12A:
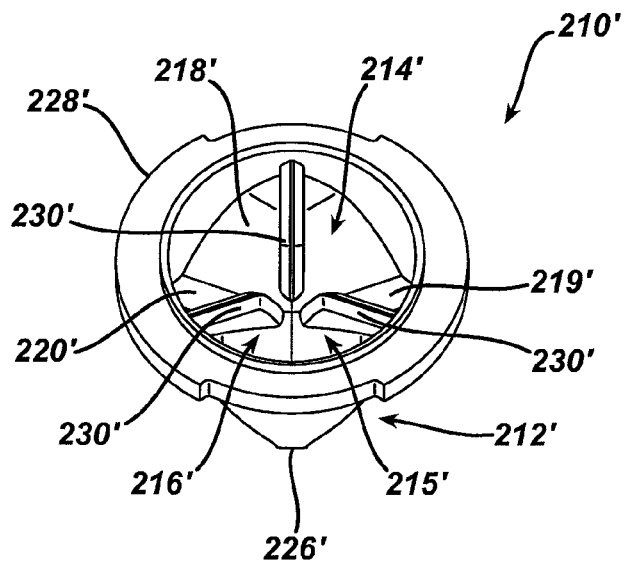
FIG. 12A is a top perspective view of another exemplary embodiment of a seal assembly.
Figure 12B:
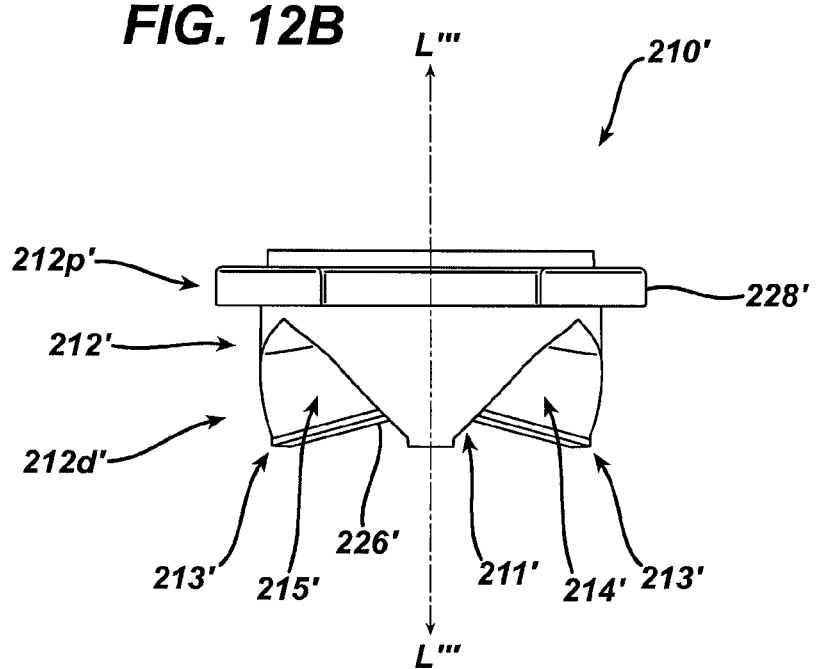
FIG. 12B is a side view of the exemplary embodiment of FIG. 12A.

An alternative design of a seal assembly that can be effective to prevent smudging on instruments inserted into and through the seal assembly is illustrated in FIGS. 12A and 12B. Similar to the seal assembly 210, the seal assembly 210' generally includes seal body 212' with a proximal end 212'p and a distal end 212'd, a longitudinal axis L''' extending through the seal body 212', and a transverse plane substantially perpendicular to the longitudinal axis L'''. As illustrated, the seal body 212' also includes a central portion 211' and a periphery portion 213'. Seal assembly 210' can include any and all of the same characteristics as discussed above with respect to seal assemblies 10, 10', 210, and similar to seal assembly 210, seal assembly 210' includes three seal elements 214', 215', 216'. The seal elements 214', 215', 216' can extend distally with respect to the transverse plane from the proximal end 212'p of the seal body 212'. The seal elements 214', 215', 216' can include inner surfaces 218', 219', 220' and outer surfaces, and in an exemplary embodiment the inner surfaces 218', 219', 220' of the seal elements 214', 215', 216' can meet at the distal end 212'd of the seal body 212' to form a seal face 226'. Further, the seal body 212' and/or the seal elements 214', 215', 216' can generally be configured to selectively open and substantially close the seal face 226'. In one embodiment the proximal end 212'p of the seal body 212' can include a flange 228' extending beyond a width of the seal body 212'.

Prevention of smudging by fluids on instruments inserted into and/or through the seal assembly 210' can be further achieved by configuring the inner surfaces 218', 219', 220' of the seal elements 214', 215', 216' such that they can selectively promote movement of fluid away from the central portion 211' of the seal body 212' and toward the peripheral portion 213' of the seal body 212'. While a variety of configurations can be used to achieve this design goal, in one embodiment the central portion 211' can be positioned such that it is more proximal than the peripheral portion 213'. In other words, as illustrated in FIG. 12B, central portion 211' is raised proximally relative to the peripheral portion 213'. Other configurations that selectively promote movement of fluid away from a central portion of a seal body are discussed in U.S. patent application Ser. No. 11/771,263 of Franer et al., filed on Jun. 29, 2007, and entitled "Duckbill Seal with Fluid Drainage Feature," which is hereby incorporated by reference in its entirety. It is understood that all of these configurations that promote movement of fluid away from a central portion of a seal body can be applied to each of the configurations discussed or referenced herein.

Similar to the seal assembly 210, the seal assembly 210' can also include one or more activation extensions. In the embodiment illustrated in FIGS. 12A and 12B, one activation extension 230' is formed on each of the three seal elements 214', 215', 216'. Although it is not necessary that an activation extension be formed on each seal element, in an exemplary embodiment, the activation extensions 230' are symmetrically placed such that when an object is placed between the activation extensions 230', the object can be equally engaged around its perimeter. Further, the activation extensions 230' can include any and all of the characteristics and features discussed above with respect to activation extensions 30, 230.

Figure 13A:
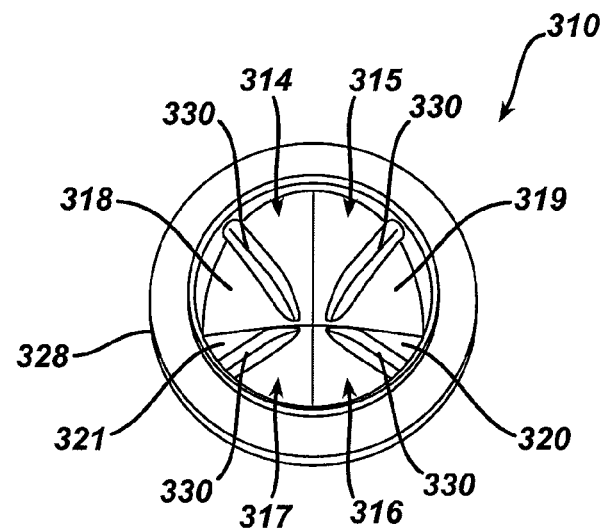
FIG. 13A is a top perspective view of another exemplary embodiment of a seal assembly.
Figure 13B:
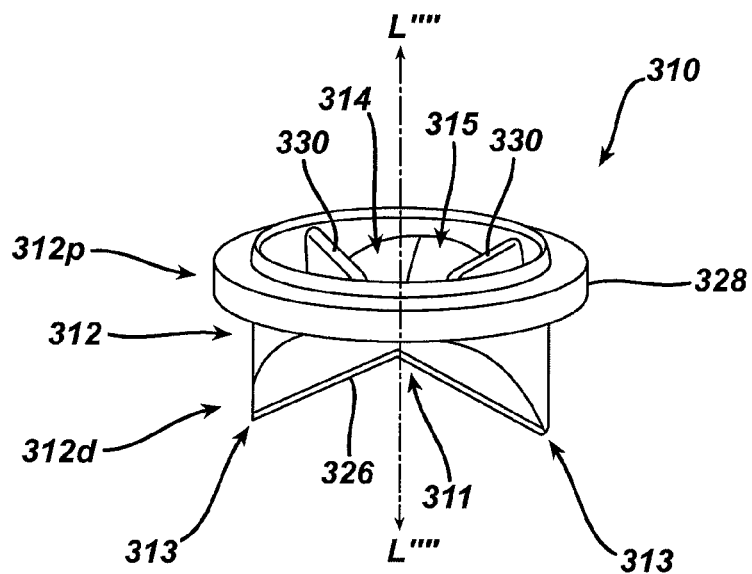
FIG. 13B is a side perspective view of the exemplary embodiment of FIG. 13A.

Still another embodiment of a seal assembly is illustrated in FIGS. 13A and 13B. In this embodiment, four seal elements are included. Similar to previous embodiments, seal assembly 310 can generally include seal body 312 with a proximal end 312p and a distal end 312d, a longitudinal axis L'''' extending through the seal body 312, and a transverse plane substantially perpendicular to the longitudinal axis L''''. As illustrated, the seal body 312 also includes a central portion 311 and a periphery portion 313. Seal assembly 310 can include any and all of the same characteristics and features as discussed above with respect to seal assemblies 10, 10', 210, 210', but while the previously illustrated embodiments included only two or three seal elements, seal assembly 310 includes four seal elements 314, 315, 316, 317. The seal elements 314, 315, 316, 317 can extend distally with respect to the transverse plane from the proximal end 312p of the seal body 312. The seal elements 314, 315, 316, 317 can include inner surfaces 318, 319, 320, 321 and outer surfaces, and in an exemplary embodiment the inner surfaces 318, 319, 320, 321 of the seal elements 314, 315, 316, 317 can meet at the distal end 312d of the seal body 312 to form a seal face 326. Further, the seal body 312 and/or the seal elements 314, 315, 316, 317 can generally be configured to selectively open and substantially close the seal face 326. In one embodiment the proximal end 312p of the seal body 312 can include a flange 328 extending beyond a width of the seal body 312.

Similar to the seal assembly 210', prevention of smudging by fluids on instruments inserted into and/or through the seal assembly 310 can be further achieved by configuring the inner surfaces 318, 319, 320, 321 of the seal elements 314, 315, 316, 317 such that they can selectively promote movement of fluid away from the central portion 311 of the seal body 312 and toward the peripheral portion 313 of the seal body 312. While any of the configurations discussed or incorporated by reference with respect to seal assembly 210' can be incorporated into the design of seal assembly 310, as illustrated the central portion 311 is raised proximally relative to the peripheral portion 313.

Figure 14A:
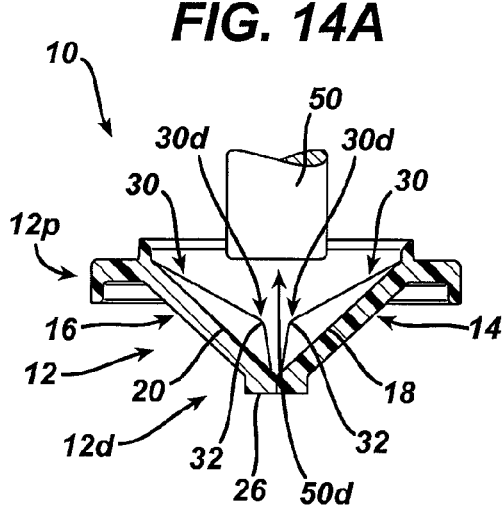
FIG. 14A is side view of the exemplary embodiment of FIG. 4 in an initial position.
Figure 14B:
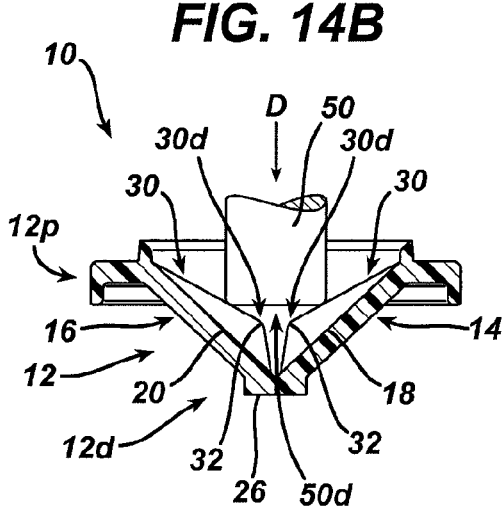
FIG. 14B is a side view of the exemplary embodiment of FIG. 4 in a contacting position.
Figure 14C:
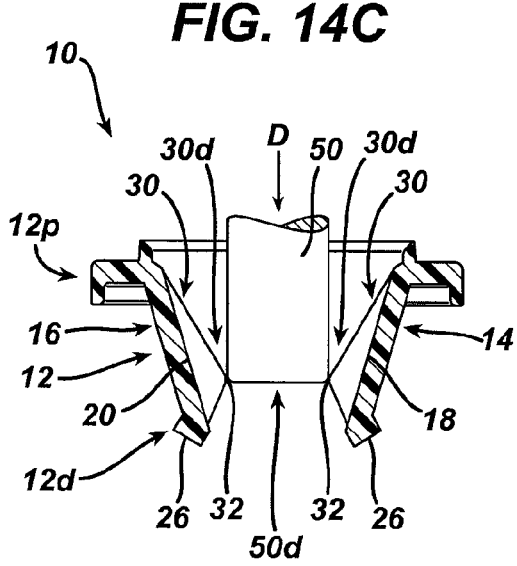
FIG. 14C is a side view of the exemplary embodiment of FIG. 4 in an opening position.

FIGS. 14A-14D illustrate the seal assembly 10 of the type shown in FIGS. 4-7 in use. In an initial position, illustrated in FIG. 14A, the seal face 26 is substantially closed and an object, such as instrument 50, is not in contact with any portion of the seal assembly 10. Turning to FIG. 14B, a force generally in a direction D is applied to the instrument 50, thus causing the instrument 50 to move toward the seal face 26 in the general direction D until a distal end 50d of the instrument 50 is in contact with at least a portion of one or more of the activation extensions 30. When the instrument 50 contacts one or more of the activation extensions 30, the duckbill seal assembly is in a contacting position. In the illustrated embodiment the instrument 50 first engages a portion of each of the proximal surfaces 38 of the activation extensions 30, but in other embodiments, the instrument 50 can first engage the distal-most end 30d or the vertex 32 of the activation extensions 30. As the force in the direction D continues to be applied to the instrument 50, the instrument 50 continues to move toward the seal face 26, as illustrated in FIG. 14C, and can result in the seal assembly 10 being in an opening position in which the seal face 26 is open, the seal elements 14, 16 move further apart than they were in the initial position, and the instrument 50 moves distally along the activation extensions 30 toward the distal-most ends 30d of the activation extensions 30. In some embodiments the instrument 50 moves distally along the activation extensions 30 and engages one or more of the distal-most ends 30 of the activation extensions 30. In other embodiments the instrument 50 may not move distally along the activation extensions 30, but application of the force in the general direction D toward the seal face 26 results in the seal face 26 opening and the seal elements 14, 16 moving further apart. Once the instrument 50 is moved to its desired location beyond the seal face 26, the seal assembly 10 can be said to be in a final position, illustrated in FIG. 14D. In the final position the seal face 26 can remain open and the seal elements 14, 16 can continue to be further apart than they were in the initial position. Additionally, while the seal elements 14, 16 can be further apart than they were in the opening position, but they do not necessarily have to be. Once the instrument 50 is done being used, it can be removed from the seal assembly 10 in much the same manner as it was introduced to the seal assembly 10.

Figure 14D:
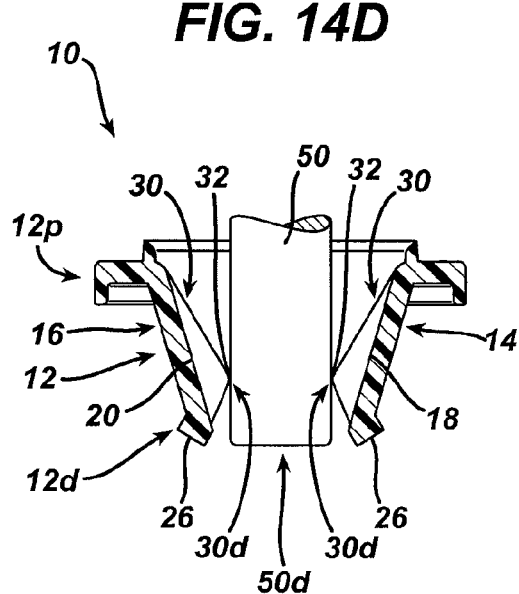
FIG. 14D is a side view of the exemplary embodiment of FIG. 4 in a final position.

Whether in the initial position, the contacting position, the opening position, or the final position, in an exemplary embodiment a system including the seal assembly 10 and the instrument 50 generally creates a closed cavity between an environment below the distal end 12d of the seal body 12 and an environment above the proximal end 12p of the seal body 12. For instance, as shown in FIGS. 14A and 14B, in both the initial and contacting positions the closed cavity is formed by the seal face 26 being substantially closed. However, as seen in FIGS. 14C and 14D, in the opening and final positions the closed cavity is formed by the seal face 26, the activation extensions 30, and the instrument 50. In other embodiments the inner surfaces 18, 20 can also help form the closed cavity. Furthermore, in instances where the cavity may not remain closed, for instance in some embodiments where two or more seal assemblies are used, the other seal assemblies can assist in creating separation between the environment below the distal end 12d of the seal body 12 and the environment above the proximal end 12p of the seal body 12.

It is understood that even though the use of seal assemblies was only discussed with respect to seal assembly 10, other embodiments of seal assemblies, for example embodiments of seal assemblies 10', 210, 210', 310 can also be used in a similar manner. Likewise, even though the trocar assembly 100 was only discussed with respect to seal assembly 10, other embodiments of seal assemblies, for example embodiments of seal assemblies 10', 210, 210', 310 can also be used in the trocar assembly 100.

A person skilled in the art will appreciate that the seal and trocar assemblies disclosed herein have application in conventional endoscopic and open surgical instrumentation as well application in robotic-assisted surgery.

The seal and trocar assemblies disclosed herein can be designed to be disposed of after a single use, or they can be designed to be used multiple times. In either case, however, the assemblies can be reconditioned for reuse after at least one use. Reconditioning can include any combination of the steps of disassembly of any or all portions of the assemblies, followed by cleaning or replacement of particular pieces, and subsequent reassembly. In particular, the assemblies can be disassembled, and any number of the particular pieces or parts of the assemblies can be selectively replaced or removed in any combination. Upon cleaning and/or replacement of particular parts, the assemblies can be reassembled for subsequent use either at a reconditioning facility, or by a surgical team immediately prior to a surgical procedure. Those skilled in the art will appreciate that reconditioning of a seal or trocar assembly can utilize a variety of techniques for disassembly, cleaning/replacement, and reassembly. Use of such techniques, and the resulting reconditioned device, are all within the scope of the present application.

Preferably, the seal and trocar assemblies described herein will be processed before surgery. First, a new or used seal or trocar assembly is obtained and if necessary cleaned. The assembly can then be sterilized. In one sterilization technique, the assembly is placed in a closed and sealed container, such as a plastic or TYVEK bag. The container and device are then placed in a field of radiation that can penetrate the container, such as gamma radiation, x-rays, or high-energy electrons. The radiation kills bacteria on the assembly and in the container. The sterilized assembly can then be stored in the sterile container. The sealed container keeps the assembly sterile until it is opened in the medical facility.

It is preferred that the assembly is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A seal for use with a seal assembly in a surgical access device, comprising:
   a seal body having two or more seal elements, the seal elements having inner and outer surfaces and meeting at a seal face at a distal end of the seal body, the seal body also having an extension protruding therefrom, the extension being configured such that an instrument passed through the seal assembly contacts the extension before contacting the seal body to open the seal assembly, and the extension having proximal and distal ends fixedly coupled to the inner surface of one of the seal elements.

2. The seal of claim 1, wherein the extension is configured such that the seal assembly opens by an instrument contacting the extension without the instrument contacting a distal end of the seal body.

3. The seal of claim 1, wherein a distal-most end of the extension is closer to a longitudinal axis extending through the seal assembly than the inner surface of the seal body.

4. The seal of claim 3, wherein a distance between the inner surface of the seal body and the distal-most end of the extension is in the range of about 0.07 inches to about 0.17 inches.

5. The seal of claim 1, wherein the distal end of the extension terminates prior to a distal end of the seal body.

6. The seal of claim 1, wherein the seal body comprises a first material and the extension comprises a second material.

7. The seal of claim 1, wherein a portion of the extension is removably and replaceably coupled to the inner surface of the seal body.

8. A surgical access device, comprising:
   a proximal housing with a cannula extending distally therefrom that is configured to extend into a body cavity, the access device including a working channel extending between the housing and the cannula that is configured to receive a surgical instrument; and
   a seal body disposed in the access device, the seal body having two or more seal elements having inner and outer surfaces and meeting at a seal face at a distal end of the seal body and also having an extension protruding therefrom that is configured such that the surgical instrument contacts the extension before contacting the seal body to open the seal body, the extension having proximal and distal ends fixedly coupled to the inner surface of one of the seal elements.

9. The surgical access device of claim 8, wherein the seal body is disposed in the cannula.

10. The surgical access device of claim 8, wherein the seal body is disposed in the housing.

11. The surgical access device of claim 8, wherein the extension is configured such that the seal body opens by an instrument contacting the extension without the instrument contacting a distal end of the seal body.

12. The surgical access device of claim 8, wherein a distal-most end of the extension is closer to a longitudinal axis extending through the working channel than the inner surface of the seal body.

13. The surgical access device of claim 12, wherein a distance between the inner surface of the seal body and the distal-most end of the extension is in the range of about 0.07 inches to about 0.17 inches.

14. The surgical access device of claim 8, wherein the distal end of the extension terminates prior to a distal end of the seal body.

15. The surgical access device of claim 8, wherein the seal body comprises a first material and the extension comprises a second material.

16. A seal for use with a seal assembly in a surgical access device, comprising:
   a seal body having an extension protruding therefrom and configured such that an instrument passed through the seal assembly contacts the extension before contacting the seal body to open the seal assembly, the extension having proximal and distal ends fixedly coupled to an inner surface of the seal body and having a portion thereof that is removably and replaceably coupled to an inner surface of the seal body.

17. The seal of claim 16, wherein the extension is configured such that the seal assembly opens by an instrument contacting the extension without the instrument contacting a distal end of the seal body.

18. The seal of claim 16, wherein a distal-most end of the extension is closer to a longitudinal axis extending through the seal assembly than the inner surface of the seal body.

19. The seal of claim 18, wherein a distance between the inner surface of the seal body and the distal-most end of the extension is in the range of about 0.07 inches to about 0.17 inches.

20. The seal of claim 16, wherein the distal end of the extension terminates prior to a distal end of the seal body.

21. The seal of claim 16, wherein the seal body comprises a first material and the extension comprises a second material.

22. The seal of claim 16, wherein the seal body is two or more seal elements having inner and outer surfaces and meeting at a seal face at a distal end of the seal body.

* * * * *